United States Patent [19]

Usami et al.

[11] Patent Number: 4,958,373
[45] Date of Patent: Sep. 18, 1990

[54] DEFECT-RECOGNITION PROCESSING APPARATUS

[75] Inventors: Toshiro Usami; Hiroyuki Kamijo, both of Yokohama; Takao Ohta, Tokyo; Masanobu Ogino, Yokosuka, all of Japan

[73] Assignee: Kabushiki Kaisha Toshiba, Kawasaki, Japan

[21] Appl. No.: 174,879

[22] Filed: Mar. 29, 1988

[30] Foreign Application Priority Data

Mar. 31, 1987 [JP] Japan .................................. 62-78659

[51] Int. Cl.$^5$ .............................................. G06K 9/00
[52] U.S. Cl. ...................................... 382/8; 358/106; 356/237
[58] Field of Search ...................... 382/2, 28; 358/106, 358/107; 250/338.4; 356/237

[56] References Cited

U.S. PATENT DOCUMENTS 4,029,962 6/1977 Chapman ......................... 250/338.4
4,764,969 8/1988 Ohtombe et al. ....................... 382/8

OTHER PUBLICATIONS

Murata et al., "A Study of Stacking Faults During CMOS Processing: Origin, Elimination and Contribution to Leakage," J. Electrochem. Soc.: Solid-State Science and Technology, vol. 127, No. 3, pp. 716-724, Mar. 1980.

Primary Examiner—Leo H. Boudreau
Attorney, Agent, or Firm—Finnegan, Henderson, Farabow, Garrett, and Dunner

[57] ABSTRACT

A defect-recognition processing apparatus converts into a defect image pattern, via a television camera, crystal defects present on the surface of an object under inspection, to process an image signal, by means of an image processing device, which corresponds to the defect image pattern, to measure rectangular images in terms of their length and their ratio between $L_Y$ and $L_X$ ($L_Y$: a length in a longitudinal direction and $L_X$: a length in the lateral direction of the wafer) and to detect defects developed on the surface of the aforementioned object.

14 Claims, 8 Drawing Sheets

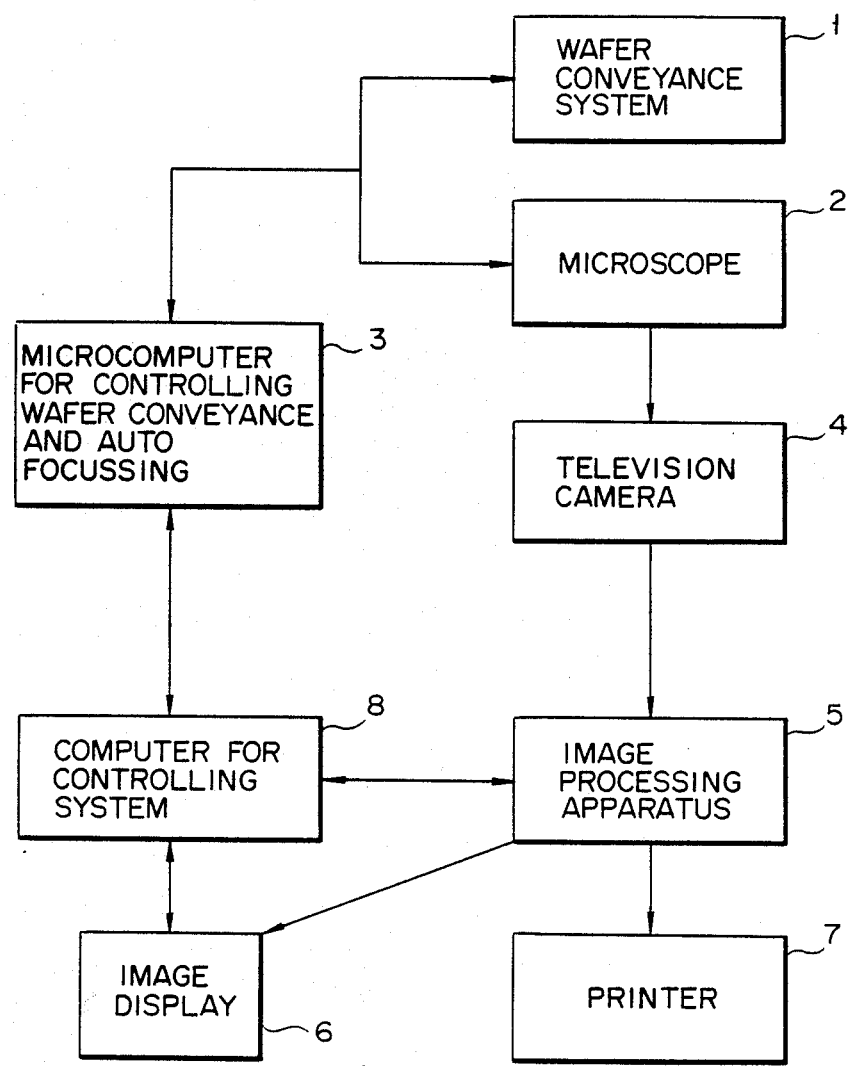
F I G. 1

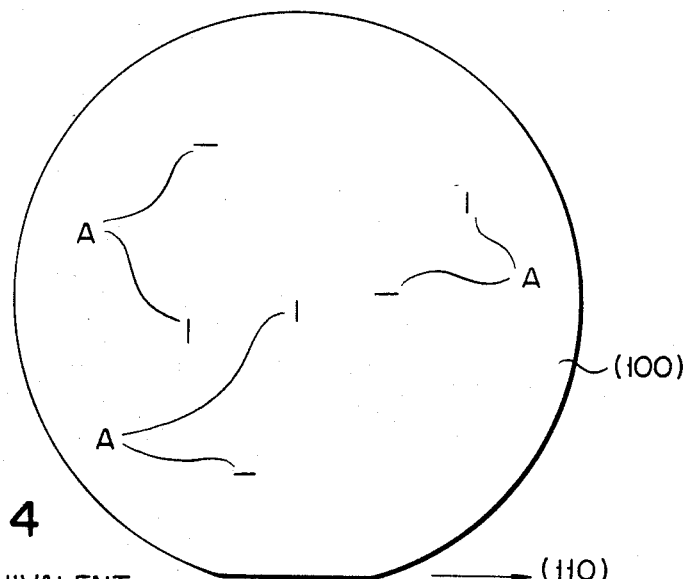
FIG. 4
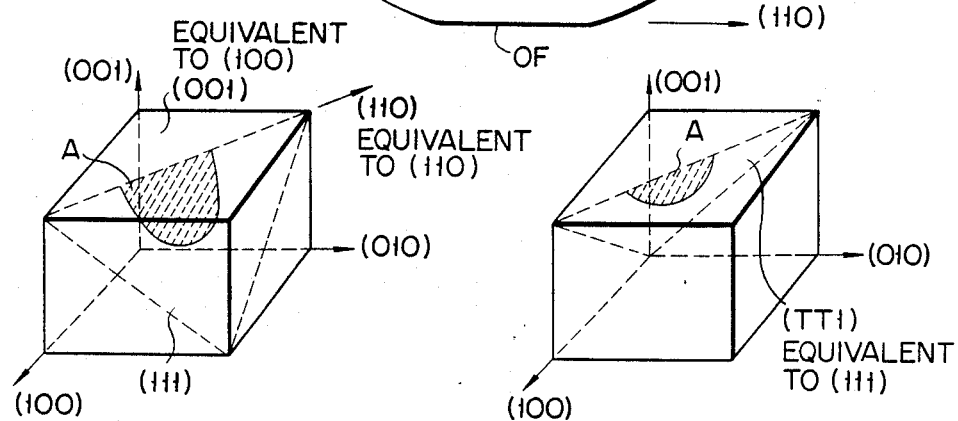
FIG. 5A  FIG. 5B
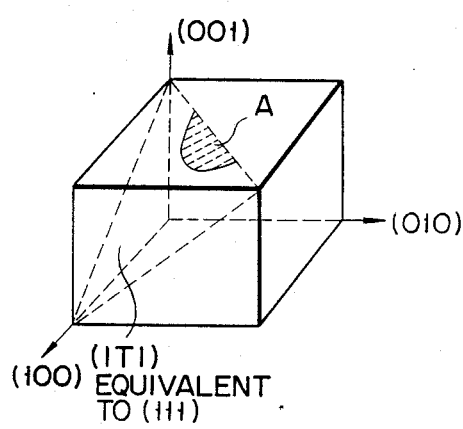 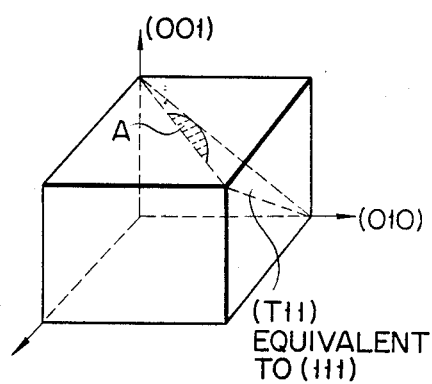
FIG. 5C  FIG. 5D

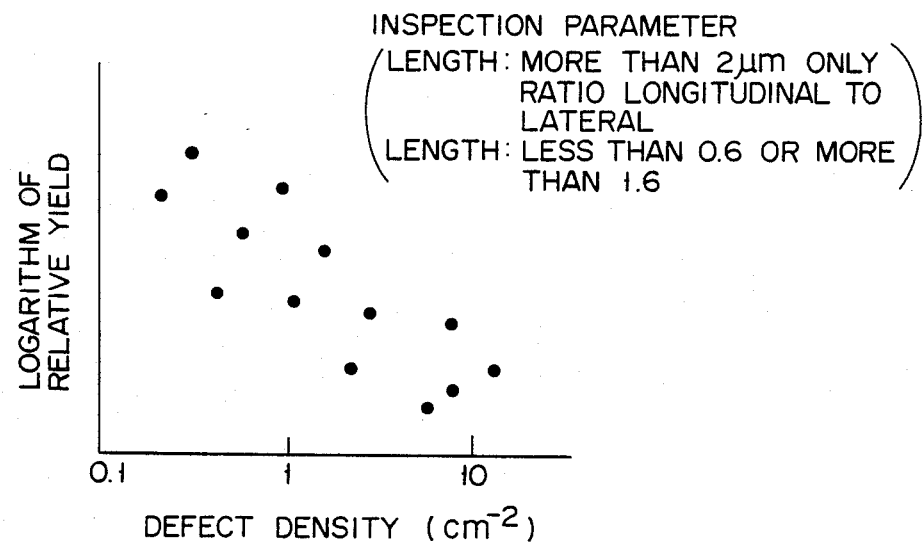
F I G. 7A
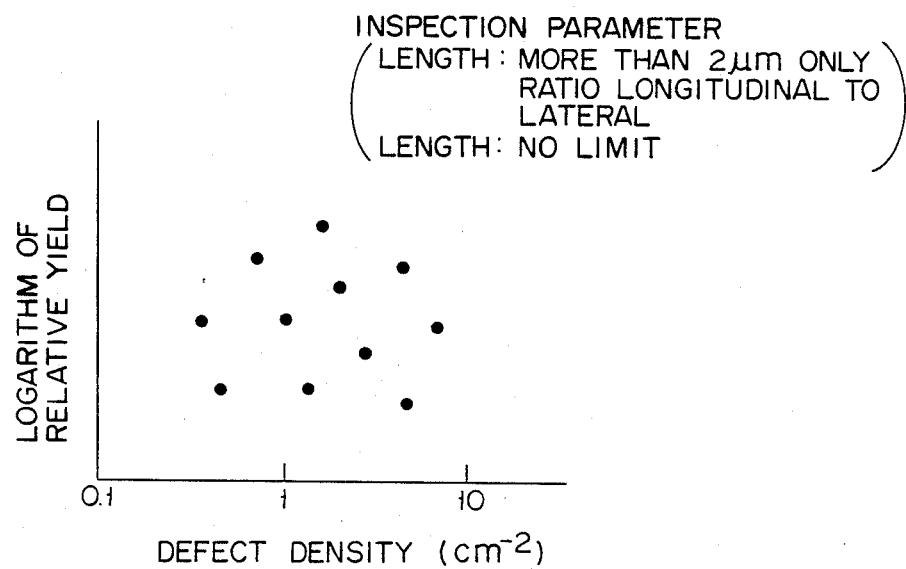
F I G. 7B

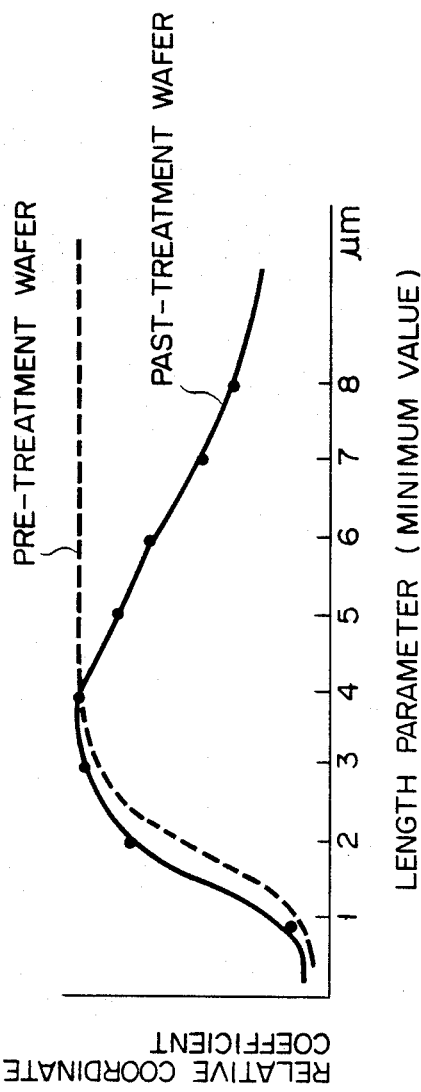
F I G. 8A
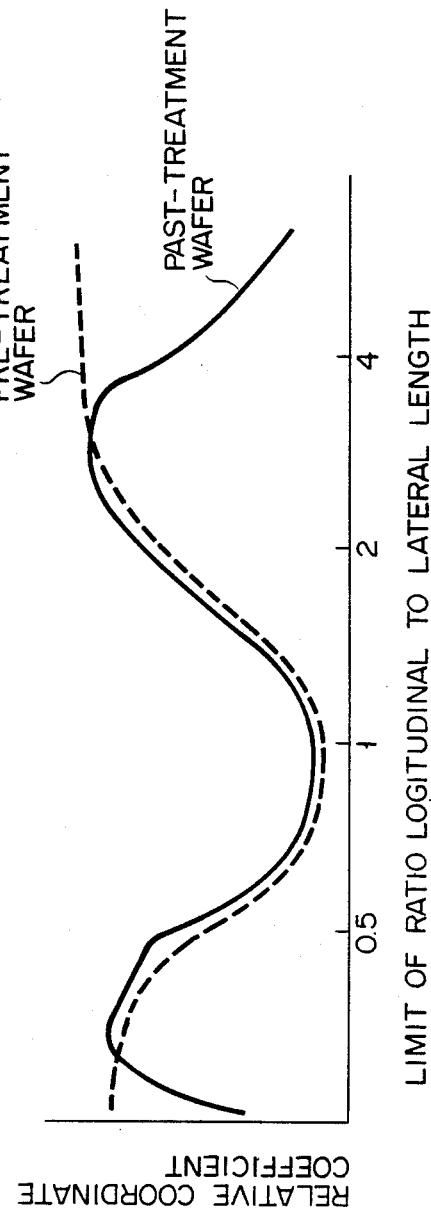
F I G. 8B

DEFECT-RECOGNITION PROCESSING APPARATUS

BACKGROUND OF THE INVENTION

1. Field of the Invention

This invention relates to a defect-recognition processing apparatus for recognizing linear crystal defects, such as stacking faults, on the surface of a semiconductor wafer.

2. Description of the Related Art

When manufacturing a semiconductor device using a silicon wafer, it is necessary to suppress the development of crystal defects, such as a dislocation or stacking fault, which cause downgrading of the electric characteristics of devices. Crystal defects occur when the arrangement of the silicon atoms in the wafer is disturbed, and are a cluster of point defects developed from the nuclei of microdefects in the wafer or from the nuclei resulting from a contamination by heavy metals at the steps of a thermal treatment, such as thermal oxidation or diffusion.

One of the quality evaluation standards for wafers is the checking or evaluation of the density of stacking faults developed on the surface of a wafer after the wafer has been oxidized. This evaluation is performed by eliminating an oxide film formed on the wafer surface, etching the wafer surface by means of a highly selective etching solution, observing the surface state under an optical microscope or a scan type electron microscope, detecting faults or defects under the configuration classification of dirt or surface scratches and counting the number of defects detected. The sizes of defects, though depending upon the heat-treatment step, are usually of the order of 0.5 to 20 μm. The size of the defects needs to be enlarged to a magnitude of about 50 × to 1000 × for observation. In order to detect the defects with high accuracy in view of the lowered control standard against the defect density (for example, 0 to 10 pieces/cm²), it is necessary to enlarge the observation area to be evaluated from the stochastic viewpoint. Thus the "gross" observation of crystal defects in reality is restricted. When the control standard value of the defect density is 100 pieces/cm², 1 piece/cm² and 0.1 piece/cm², it is possible to accurately control the defect density by observing the microscopic field view of over 1/100 cm², over 1 cm² and over 10 cm², respectively. It takes about one second per field to recognize defects. Thus it takes about 2 to 5 hours per piece of a silicon wafer 125 mm in diameter. Where a great number of silicon wafers are to be processed, a great variation (× 2 to 4) in the results of observation occurs due to the physical limitations, such as the eye-strain and disturbed concentration of the observer, failing to make proper observation.

A defect-recognition processing apparatus has been proposed which picks u an image corresponding to that area of the wafer which is being enlarged by the microscope, and detects a defect image on the image screen through pattern recognition. However, the apparatus suffers from disadvantages from the standpoint of utility, such as a lowered rate of recognition, a lowered processing speed, and high manufacturing cost. The term "the rate of recognition" means:

$$\frac{\text{total number of defects} - \text{number of defects recognized}}{\text{total number of defects}}$$

The same characteristic can equally be true of not only defects on the surface of the semiconductor wafers but also defects on the surface of other objects, such as metal.

SUMMARY OF THE INVENTION

The present invention relates to a defect-recognition processing apparatus which is low in manufacturing cost, high in the speed of recognition and in the processing speed.

The defect-recognition processing apparatus of the present invention comprises an image converting unit for converting, to an image, surface data corresponding to a predetermined area on the surface of an object being inspected, an image processing unit for processing an image signal coming from the image converting unit to detect a defect image, and a system control unit for controlling the operations of the image processing unit and associated units.

The defect-recognition processing apparatus of the present invention includes means for converting, to a defect image pattern by an image conversion unit, a defect on the surface of an object being inspected, and means for processing by means of an image-processing unit, an image signal corresponding to the defect image pattern from the image conversion unit, to measure parameters, such as the length of a rectangular image and the ratio of lateral length to longitudinal length of the defect, and to detect the presence of defects on the surface of the object being inspected.

According to the present invention, the defect on the surface of the object being inspected is image-processed and the length of a rectangular defect image and the aforementioned ratio of lateral length to longitudinal length are measured in order to evaluate the presence of the defect. The apparatus of the present invention can further assure a simple processing program and is low in manufacturing cost, and high in the processing speed and in the rate of recognition.

BRIEF DESCRIPTION OF THE DRAWINGS

FIG. 1 is a block diagram showing a defect-recognition processing apparatus according to one embodiment of the present invention;

FIG. 4 is a plan view showing an example of a semiconductor wafer to be inspected by means of the defect-recognition processing apparatus of FIG. 1;

FIGs. 5A to 5D are each a model for explaining a stacking fault on a (100) face of a silicon crystal;

FIGS. 7A and 7B are each a relative correlation between defect density and yield when measurement parameters vary;

FIG. 8A shows a relation of a relative coefficient to the parameter of a defect length, and FIG. 8B shows a relation of a relative coefficient to a ratio of a longitudinal to a lateral length of a defect;

DETAILED DESCRIPTION OF THE PREFERRED EMBODIMENTS

Figure 2:
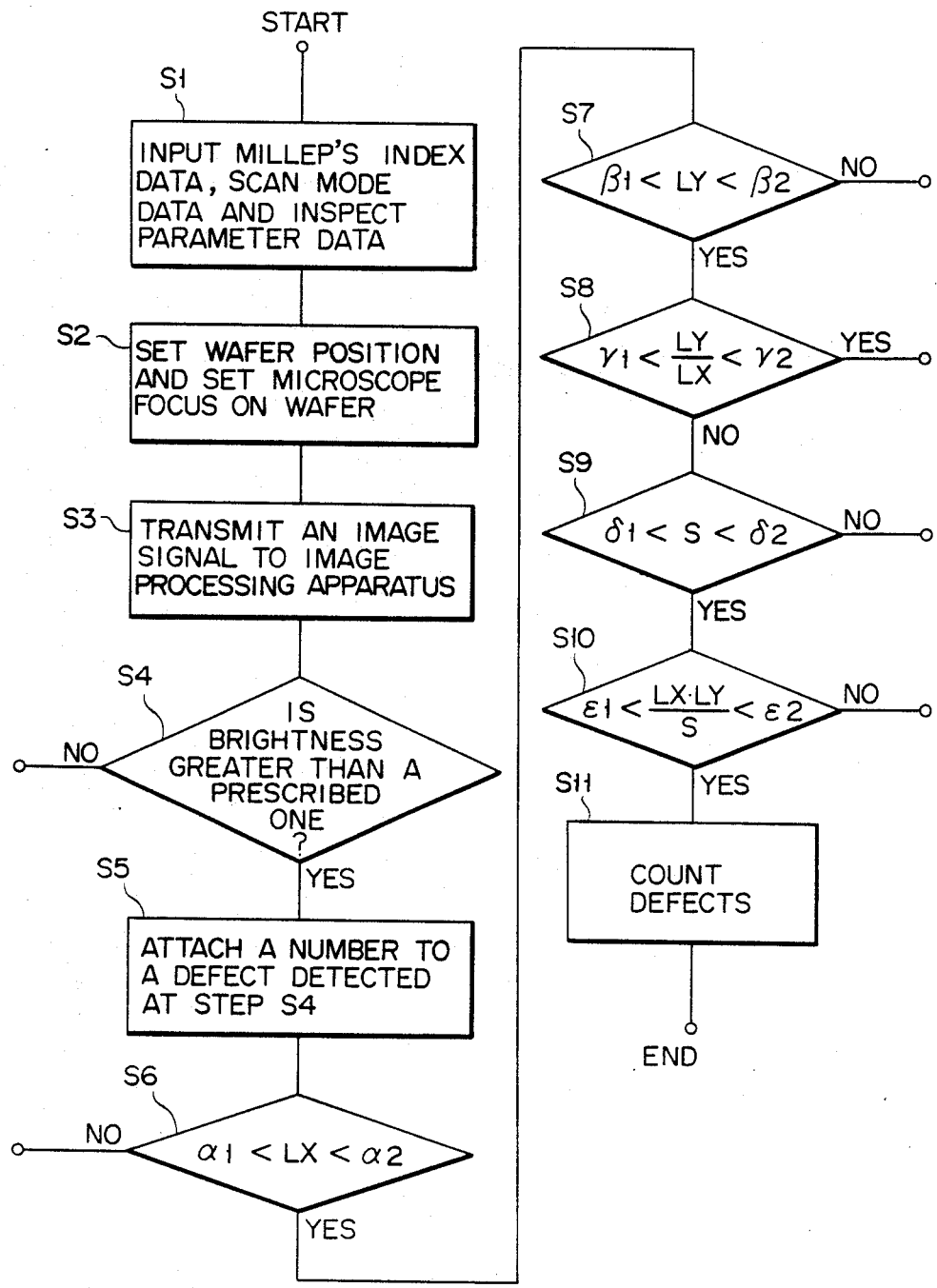
FIG. 2 is a flowchart for performing the defect-recognition processing according to the defect-recognition processing apparatus of the present invention.

A defect recognition-processing apparatus according to an embodiment of the present invention will now be explained below, with reference to the accompanying drawings.

FIG. 1 shows an apparatus for recognition-processing, for example, crystal defects in a semi-conductor wafer. Reference numeral 1 shows a wafer conveyance system and numeral 2 shows a microscope for enlarging and imaging a predetermined area on a surface of the wafer conveyed from wafer conveyance system 1 onto a movable stage. Microscope 2 has, for example, a magnification factor of 100 ×, achieved by a combination of an object lens of 10 × magnification and an eyepiece also of 10 × magnification. Microcomputer 3 performs conveyance control of conveyance system 1 and autofocussing control of microscope 2, and television camera 4 converts an image formed on microscope 2 into a TV image. Image processing apparatus 5 is provided for the binary conversion of a TV image signal, for the measurement of an image length, for example, in the X- and Y-direction, and for the detection of defect images and the counting of defects or faults. The image processing apparatus feeds the television image to image display 6 and supplies a result of the processing to printer 7. Computer 8 controls the system of the defect recognition-processing apparatus in a coordinating fashion and allows a transfer of control data among image processing apparatus 5, image display 6 and microcomputer 3.

The operation of the defect recognition-processing apparatus according to the present invention will now be explained with reference to the flowchart of FIG. 2.

Figure 3A:
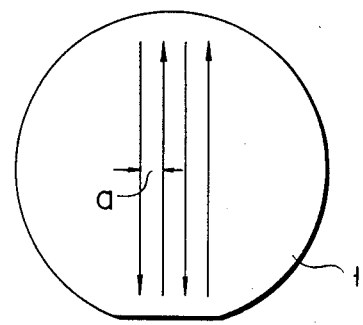
FIGS. 3A to 3C show various modes of examination made by the defect-recognition processing apparatus.
Figure 3B:
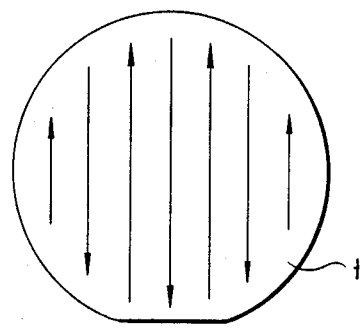
Figure 3C:
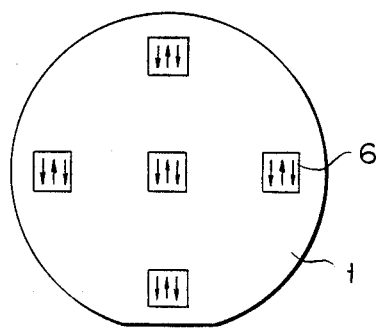

In step $S_1$, data (Miller's index data) on the crystal face of the semiconductor wafer being inspected, as well as scan mode data on the TV camera, is input to computer 8. The scan mode, as is shown in FIGS. 3A to 3C, includes (1) a coordinate designation checking mode, which is a mode for designating a position on the coordinates at which scanning is started on semiconductor wafer 1 and for designating the number of scans and the scanning spacing, shown in FIG. 3A; (2) a whole-surface checking mode, which is a mode for designating the number of scans over the semiconductor wafer, shown in FIG. 3B; and (3) a ROI (region of interest) checking mode, which is a mode for designating the number of scans at the checking or measuring spots 6, shown in FIG. 3C.

Binary data is input to computer 8 so as to check whether a defect image emerging as a microscopic image is a true crystal defect while using a shade image as checking parameters against the presence of crystal defects or dirt and dust.

As the checking or evaluation parameters, $\alpha_1 < L_X < \alpha_2$ and $\beta_1 < L_Y < \beta_2$ are input to computer 8 where $L_X$ denotes the length of a crystal defect on the X-coordinate and $L_Y$ denotes the length of the crystal defect on the Y-coordinate.

Data $\gamma_1 < L_Y/L_X < \gamma_2$ is input as the checking data to computer 8 to evaluate $\gamma_1 < L_Y/L_X < \gamma_2$. Data $\delta_1 < S < \delta_2$ is also input to computer 8 where S represents an area S of the crystal defect.

Data $\epsilon_1 < L_X \cdot L_Y/S < \epsilon_2$ is input to computer 8 to evaluate the expression for a rectangular area $L_X \times L_Y$, on the X, Y coordinates, of the crystal defect.

At step $S_2$, the semiconductor wafer is set to a predetermined position by wafer conveyance system 1 whose operation is controlled by microcomputer 3. The semiconductor wafer thus set is minutely moved or turned in the X- or Y-direction, to an exact position so as to pick up an image observed under the microscope. Furthermore, the semiconductor wafer is moved up and down to meet the microscopic focus. At this time, the visual field of the microscope is, for example, 0.7 mm in the longitudinal direction and 0.525 mm in the lateral direction, noting that the microscope has an amplification 100 × with an eyepiece of an amplification 10 × and an object lens of an amplification 10 × and that an image size to be checked is 0.56 mm×0.5 mm.

At step $S_3$, the microscopic image picked up by TV camera 3 is transferred as an image signal to image processing apparatus 5. At step $S_4$, the image signal has its shade image converted by image processing apparatus 5 to binary data with a predetermined brightness level as a reference. In this case, an image level which is greater than the predetermined brightness level is left as corresponding to the defect image being inspected. At step $S_5$, of those binary-converted images, those left as the defect images are numbered, that is, the numbers (NOs) are attached to the defect images.

At step $S_6$, the expression $\alpha_1 < L_X < \alpha_2$ is evaluated, at step $S_7$ the expression $\beta_1 < L_Y < \beta_2$ is checked and at step $S_8$ the expression $\gamma_1 < L_Y/L_X < \gamma_2$ is evaluated. When no defect is detected, the process shifts to step $S_9$. At step $S_9$, the defect surface area S is evaluated as to whether or not it is within a predetermined range $\delta_1 < S < \delta_2$. At step $S_{10}$, the expression $\epsilon_1 < L_X \cdot L_Y/S < \epsilon_2$ is evaluated.

Figure 6:
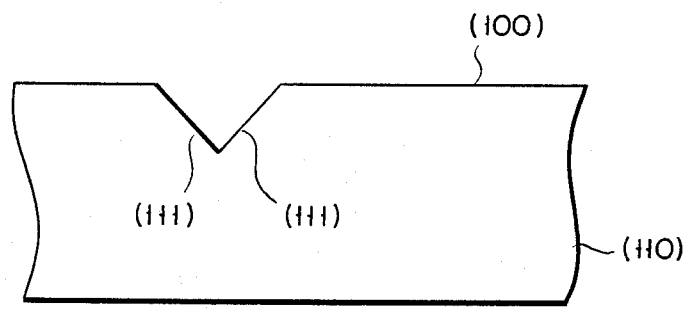
FIG. 6 is a cross-sectional view showing a stacking fault on the (100) face of the silicon crystal.

At these steps $S_6$ to $S_{10}$, the defect images satisfying the expressions are picked up as corresponding to true defects and at step S11 their number is counted. For evaluation, wafers were prepared by diffusing an impurity into well regions during the manufacture of, for example, CMOS type LSIs (memories, CPUs, etc.), removing all of an oxide film from some wafers, picked up from a lot, with the use of an NH$_4$F solution and selectively etching crystal defects on the wafer with the use of a light etching solution. In this case, the wafer had a (100) face as a major surface and, if the orientation flat (OF), that is, one side face of a single crystal rod, which provided a reference face for determining the crystallographic orientation, was formed in a <110> direction, stacking faults A were developed in the horizontal or the vertical direction, as shown in FIG. 4. That is, as shown in FIGS. 5A to 5D, the stacking faults on the surface of a silicon substrate were developed within the plane of a crystallographic Si face (111) or within the plane of an equivalent face. From FIG. 6 it will be appreciated that the cross-section of the wafer at the plane of the crystal face (111) is V-shaped which is surrounded with the (111) crystal plane. It is observed that, on the surface of the silicon substrate with the (100) crystal face as a major surface, stacking faults were developed linearly in the <110> direction or in the equivalent direction. Since the orientation flat parallel to the <110> direction was formed on the wafer with the (100) face as the major surface of the substrate, the stacking faults extended parallel or perpendicular to the orientation flat.

Checking was made for the defects or faults of the wafers being inspected with the use of the aforementioned various checking parameters and the defect density was found. For the defect density measured by the checking parameters and a final yield in an original lot from which the aforementioned wafers were picked up, their relative coefficient was found to obtain data as shown in FIGS. 7A and 7B. When the length parameter and $\gamma_1 < L_Y/L_X < \gamma_2$ parameter were optimized after the relative coefficient had been obtained against the various parameters, then the relative correlation coefficient was obtained as indicated by the solid lines in FIGS. 8A and 8B. In this case, as the possible causes for development of defect spots on the wafer surface, the defect nuclei in posttreatment wafers and contamination of the wafer with a heavy metal during the manufacture of a semiconductor device are included. In order to eliminate the causes for defects or faults, some pretreatment wafers were picked up and thermally oxidized, for example, at 1000° C. for 10 hours so as to perform a pretest. Upon evaluation of that pre-test, the relation of the relative correlation coefficient to the defect density was obtained as indicated by the dotted lines in FIGS. 8A and 8B.

In the case where the major surface of the semiconductor wafer being inspected was a (100) face, only those defects longer in the <110> direction were detected, their density was found, and a value corresponding to double that density was output as the crystal defect density. In the case where the major surface of the semiconductor wafer was in the (111) direction, only those defects longer in the <110> direction were detected, their density was found, a value corresponding to three times that density was output as a crystal defect density.

From the foregoing it has been found that, for the defect length of over about 2 μm as the reference of measurement its relative correlation coefficient to a final yield of wafers was improved. It has also been found that, if $\gamma_1 < L_Y/L_X < \gamma_2$ as the reference of measurement was in a range of over 1.6 or below 0.6, its relative correlation coefficient to the final yield was improved. The same results were also obtained by conducting tests in the manufacturing steps of wafers which may involve a contamination problem. However, it is not clear in detail as to why such relation is generally obtained. It is believed that it will be appreciated that, for a smaller defect, no bad influence is exercised over semiconductor elements if an electronic charge on that defect spot is small and that, while a design rule is maintained, no bad effect is exercised over those regions which would otherwise cause defects in terms of their element characteristics. If the crystal face was restricted to a direction equivalent to the <110> direction, then a further improvement was obtained in the correlation coefficient of the defect density and in the final yield.

In view of the fact that a ready image processing is obtained by setting the horizontal scanning direction of the TV image in a direction parallel to, or perpendicular to, one face of the defect spot, it is desirable to support the orientation flat OF of the wafer on a wafer support pedestal, for example, in a direction parallel to the horizontal scanning direction of TV camera 4, to measure the density of defects in that horizontal scanning direction and to measure the density of defects in the horizontal scanning direction with the wafer turned in a vertical direction.

Figure 9:
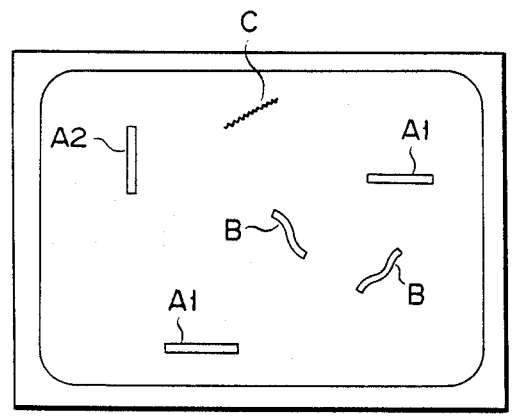
FIG. 9 is a view showing a model of defect images obtained from the defect-recognition processing apparatus of FIG. 1.

FIG. 9 shows one example of an image which was displayed, as the result of image processing, on display unit 6 in the defect-recognition processing apparatus. In those images $A_1$ and $A_2$ extending in the horizontal and vertical scanning directions on the screen of the display unit, stacking fault images are contained and thus if a recognition processing program is given to the apparatus so as to detect some of images extending in the horizontal or vertical direction, for example, those images of $\gamma_1 < L_Y/L_X < \gamma_2$ whose ratio is over 1.6 or under 0.6, then it is possible to distinguish the image from dirt B or scar C. When, in this case, there were 10 stacking faults per image screen of the display unit, 0.8 seconds were taken as the recognition processing time. It has been proved possible to support the wafer with the orientation flat OF of the wafer oriented in a direction parallel to the horizontal scanning direction, to find the density of defects through the image processing of defects longer in the <110> direction, and to deliver, as the result of measurement, an output corresponding to double the aforementioned defect density in which case the density of defects longer in the direction perpendicular to the <110> direction is regarded as being substantially equivalent to that in the aforementioned <110> direction. It is thus possible to reduce the time of measurement.

Although in the aforementioned embodiment the wafer has been explained as being oriented in a direction parallel to that of the orientation flat of the wafer, the same effect as set forth in connection with the aforementioned embodiment is obtained if the wafer is located in a direction perpendicular to the orientation flat of the wafer. If the wafer is so located as to allow the orientation flat of the wafer to be arranged in an irregular direction to the horizontal scanning direction of TV camera 4, then the stacking defect image becomes deviated from the horizontal scanning direction. However, the defects can be detected by detecting those images whose length is over 2.0 μm and whose ratio $\gamma_1 < L_Y/L_X < \gamma_2$ is within a range of over 1.6 or under 0.6.

Figure 10:
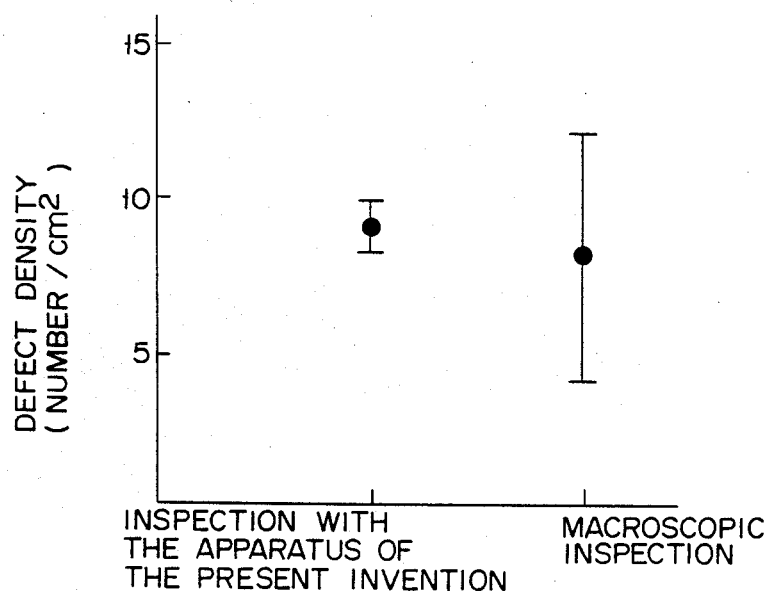
FIG. 10 is a comparison between the measurement data of a defect density detection reproducibility by the defect-recognition processing apparatus and that observed "grossly"

In the defect-recognition processing apparatus of the present invention, it is possible to readily detect the stacking faults of the semiconductor wafer and to make a continuous quality check against lots of wafers. In this way, it is possible to simply, but highly accurately, make a check on the surface of semiconductor wafers and semiconductor elements in the manufacture step, to do the control of defect wafers and the contamination of wafers within a heat processing furnace and to improve the quality and yield of devices. In this connection it is to be noted that when silicon substrates 125 mm in diameter were examined with the use of the aforementioned processing apparatus the defect-recognition processing time per wafer for a stacking fault density of about 10 pieces/cm$^2$ was about 4 minutes, a value reduced to about one-fourth the value (15 minutes) observed "grossly". Furthermore, the defect detection reproduction was improved as shown in FIG. 10 in which case a variation in the defect detection reproduction was ~1/5 in comparison with a value observed "grossly".

Although in the aforementioned embodiment the (100) face wafer has been explained as having a (100)

major surface, it has been proved possible to automatically measure and detect only crystal defects longer in the (110) face or in the equivalent direction in the case of wafers having a (111) face and to find their density. It has also been proved possible to evaluate the density of defects in the <110> direction or in one of equivalent directions and to deliver an output, as a result of defect density measurement, corresponding to three times the aforementioned density.

If not only stacking faults but also a stepped surface of the wafer is produced in the photoetching and forming processes of the wafers, it is desirable to add to the apparatus a step pattern eliminating feature so that, in order to convert an image signal to a binary one, defect detection may be made after the elimination of an image pattern which is generated from the aforementioned stepped surface of the wafer. Thus the image processing time can be reduced.

Figure 11:
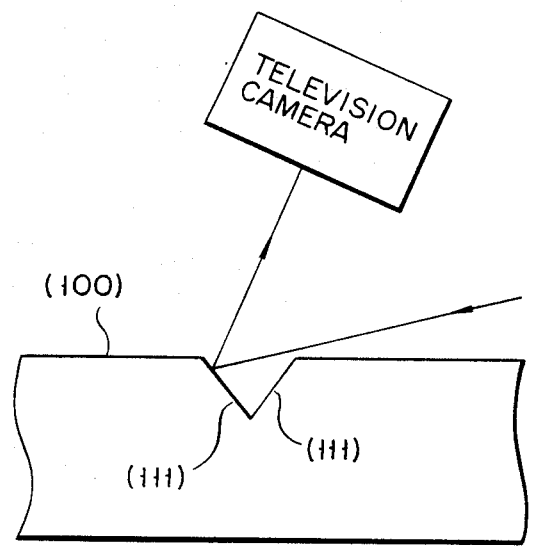
FIG. 11 is a view showing an arrangement between an illumination unit upon the illumination of a stacking fault developed on the surface of a semiconductor wafer by light and a high receiving unit.

Although, in the aforementioned embodiment, the image processing has been explained as being performed after the illumination of the wafer surface with light and the conversion of reflected light to an image signal, the detection percentage of defects can be enhanced by illuminating the defects on the wafer surface with light and receiving the reflected light. As shown in FIG. 11, for example, the stacking faults of the (100) face of the wafer are developed in a laminar fashion and, if light is directed on the wafer surface diagonally from above, the light reflected from the stacking faults on the (111) face of the wafer is strong but the light reflected from the dirt or scars on the wafer surface is weak and can be eliminated from the evaluation of the image processing. As a result, the stacking faults can be efficiently image-processed, detected and counted. Since the (111) face of the wafer is oriented at an angle of 54° to the (100) face of the wafer, if the light is made incident at an angle of, for example, 80° to the (100) face of the wafer, a light reception unit (the object lens of the microscope) needs only to be set in a "28°" position so that reflected light from the (111) face of the wafer can properly be detected. The angle of incidence to the (100) face of the wafer is within a range from over 54° to under 90°. The object lens is located at an angle of $108° - \theta$ at which light is reflected from the (111) surface of the wafer. The angle of incidence of reflected light should be made as great as desirable because the focus of the microscope is not shifted within a visual field. In order to separate a stacking-fault image of high signal level and a dirt/scar image of low signal level from the reflected image, the reflected image is converted to a binary image to provide a shade image. It is thus possible to detect, as the stacking-fault image, an image higher in contrast than the background.

The present invention is also applicable to the detection of crystal defects on the semiconductor wafer surface as well as rectangular defects on the wafer surface developed in a predetermined direction. Thus the present invention can find a wider field of application.

What is claimed is:

1. A defect-recognition processing apparatus comprising:
    image converting means for converting, into an image, surface data corresponding to a predetermined area on a surface of an object being inspected;
    image processing means for processing the image from said image converting means and for detecting the presence of a defect image having both a length greater than a predetermined value and a ratio $L_y/L_X$ having a value greater than n or a value lower than 1/n where $L_Y$ denotes a length of the defect image in a longitudinal direction and $L_X$ denotes a length of the defect image in a lateral direction; and
    system control means for controlling operations performed by said image processing means.

2. A defect-recognition processing apparatus according to claim 1, wherein said object is a semi-conductor wafer.

3. A defect-recognition processing apparatus according to claim 1, wherein said rectangular image has a length greater than 2 μm and said ratio $L_Y/L_X$ is in a range of a value greater than 1.6 or lower than 0.6.

4. A defect-recognition processing apparatus according to claim 1, wherein a horizontal TV scanning direction corresponds to a direction parallel to or perpendicular to one side of said rectangular image.

5. A defect-recognition processing apparatus according to claim 1, wherein said object is a silicon wafer having a (100) face as a major surface and an orientation flat in a <110> direction and only those defects longer in the <110> or the equivalent direction are detected.

6. A defect-recognition processing apparatus according to claim 5, wherein a horizontal TV scanning is performed in a direction horizontal to or perpendicular to said orientation flat.

7. A defect-recognition processing apparatus according to claim 5, wherein those defects longer in said <110> direction are detected to find a defect density, and a signal corresponding to double said defect density is output as a crystal defect density.

8. A defect-recognition processing apparatus according to claim 1, wherein said object has a (111) face as a major surface and only those defects longer in the <110>, or the equivalent direction are detected.

9. A defect-recognition processing apparatus according to claim 5, wherein those defects longer in said <110> direction are detected to obtain a defect density, and an output corresponding to three times said defect density is delivered as a crystal defect density.

10. A defect-recognition processing apparatus according to claim 1, wherein said object is a silicon wafer having a stepped pattern on the surface, and said image processing means converts the picked-up TV signal to a binary signal and detects defects after elimination of an image pattern formed by said stepped pattern.

11. A defect-recognition processing apparatus according to claim 1, wherein said image converting means illuminates a flat surface of said object with light coming diagonally from above, and receives reflected light to be picked up as TV data.

12. A defect-recognition processing apparatus according to claim 1, wherein said object is a silicon wafer having a (100) face as a major surface and light is received which is reflected from the (100) face of the silicon wafer surface.

13. A defect-recognition processing apparatus according to claim 12, wherein light is incident on said (100) face of said silicon wafer at an angle of $54° < \theta < 90°$, and is reflected, at an angle of $108° - \theta$, on that light reflection face.

14. A defect-recognition processing apparatus according to claim 1, wherein said image processing means detects an image signal, as said picked-up TV signal, in the form of a shade image and an image different in brightness level from a background as a stacking fault.

* * * * *